United States Patent
Plotkin et al.

(10) Patent No.: US 9,597,521 B2
(45) Date of Patent: Mar. 21, 2017

(54) TRANSMITTING COILS FOR NEUROSTIMULATION

(71) Applicant: BlueWind Medical Ltd., Herzliya (IL)

(72) Inventors: Anton Plotkin, Tel Aviv (IL); Guri Oron, Tel Aviv (IL)

(73) Assignee: BLUEWIND MEDICAL LTD., Herzliya (IL)

( * ) Notice: Subject to any disclaimer, the term of this patent is extended or adjusted under 35 U.S.C. 154(b) by 0 days.

(21) Appl. No.: 14/601,568

(22) Filed: Jan. 21, 2015

(65) Prior Publication Data
US 2016/0206889 A1    Jul. 21, 2016

(51) Int. Cl.
*A61N 1/362* (2006.01)
*A61N 1/378* (2006.01)
*A61N 1/36* (2006.01)

(52) U.S. Cl.
CPC ....... *A61N 1/3787* (2013.01); *A61N 1/36125* (2013.01)

(58) Field of Classification Search
CPC ............ A61N 1/37223; A61N 1/37229; A61N 1/3787
See application file for complete search history.

(56) References Cited

U.S. PATENT DOCUMENTS

| | | | |
|---|---|---|---|
| 3,411,507 A | 11/1968 | Wingrove | |
| 3,693,625 A | 9/1972 | Auphan | |
| 4,019,518 A | 4/1977 | Maurer et al. | |
| 4,338,945 A | 7/1982 | Kosugi et al. | |
| 4,392,496 A | 7/1983 | Stanton | |
| 4,535,785 A | 8/1985 | Van Den Honert | |
| 4,559,948 A | 12/1985 | Liss et al. | |
| 4,573,481 A | 3/1986 | Bullara | |
| 4,585,005 A | 4/1986 | Lue et al. | |
| 4,602,624 A | 7/1986 | Naples | |
| 4,608,985 A | 9/1986 | Crish | |

(Continued)

FOREIGN PATENT DOCUMENTS

| | | |
|---|---|---|
| EP | 0 688 577 | 12/1995 |
| EP | 1533000 | 5/2005 |

(Continued)

OTHER PUBLICATIONS

Reggiani et al. "Biophysical effects of high frequency electrical field on muscle fibers in culture." (2009) pp. 49-56.
(Continued)

*Primary Examiner* — George Evanisko
(74) *Attorney, Agent, or Firm* — Sughrue Mion, PLLC (57) ABSTRACT

Apparatus and methods are described, including a medical implant that includes a receiving coil. A transmitting device includes a first transmitting coil, and a second transmitting coil disposed with respect to the first transmitting coil such that a shortest distance from an edge of the second transmitting coil to an edge of the first transmitting coil is within 20% of a length of the receiving coil. A control unit is configured to transmit power to the medical implant by driving a current source to drive a current in a clockwise direction through one of the transmitting coils, and drive a current in a counterclockwise direction through the other one of the transmitting coils. Other applications are also described.

17 Claims, 3 Drawing Sheets

(56) References Cited

U.S. PATENT DOCUMENTS

| | | |
|---|---|---|
| 4,628,942 A | 12/1986 | Sweeney |
| 4,632,116 A | 12/1986 | Rosen |
| 4,649,936 A | 3/1987 | Ungar |
| 4,663,102 A | 5/1987 | Brenman et al. |
| 4,739,764 A | 4/1988 | Lue |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,069,680 A | 12/1991 | Grandjean |
| 5,178,161 A | 1/1993 | Kovacs |
| 5,188,104 A | 2/1993 | Wernicke |
| 5,199,428 A | 4/1993 | Obel et al. |
| 5,199,430 A | 4/1993 | Fang |
| 5,203,326 A | 4/1993 | Collins |
| 5,205,285 A | 4/1993 | Baker, Jr. |
| 5,215,086 A | 6/1993 | Terry, Jr. |
| 5,263,480 A | 11/1993 | Wernicke |
| 5,282,468 A | 2/1994 | Klepinski |
| 5,292,344 A | 3/1994 | Douglas |
| 5,299,569 A | 4/1994 | Wernicke |
| 5,314,495 A | 5/1994 | Kovacs |
| 5,330,507 A | 7/1994 | Schwartz |
| 5,335,657 A | 8/1994 | Terry, Jr. |
| 5,411,535 A | 5/1995 | Fujii et al. |
| 5,423,872 A | 6/1995 | Cigaina |
| 5,439,938 A | 8/1995 | Snyder et al. |
| 5,454,840 A | 10/1995 | Krakovsky et al. |
| 5,487,760 A | 1/1996 | Villafana |
| 5,505,201 A | 4/1996 | Grill, Jr. |
| 5,540,730 A | 7/1996 | Terry, Jr. |
| 5,540,733 A | 7/1996 | Testerman et al. |
| 5,540,734 A | 7/1996 | Zabara |
| 5,549,655 A | 8/1996 | Erickson |
| 5,571,150 A | 11/1996 | Wernicke |
| 5,591,216 A | 1/1997 | Testerman et al. |
| 5,634,462 A | 6/1997 | Tyler et al. |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry, Jr. |
| 5,711,316 A | 1/1998 | Elsberry et al. |
| 5,716,385 A | 2/1998 | Mittal |
| 5,755,750 A | 5/1998 | Petruska |
| 5,776,170 A | 7/1998 | Macdonald et al. |
| 5,776,171 A | 7/1998 | Peckham |
| 5,814,089 A | 9/1998 | Stokes |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,861,019 A | 1/1999 | Sun et al. |
| 5,916,239 A | 6/1999 | Geddes et al. |
| 5,938,584 A | 8/1999 | Ardito et al. |
| 5,944,680 A | 8/1999 | Christopherson |
| 5,954,758 A | 9/1999 | Peckham |
| 5,991,664 A | 11/1999 | Seligman |
| 6,002,964 A | 12/1999 | Feler et al. |
| 6,026,326 A | 2/2000 | Bardy |
| 6,026,328 A | 2/2000 | Peckham |
| 6,032,076 A | 2/2000 | Melvin et al. |
| 6,058,331 A | 5/2000 | King et al. |
| 6,066,163 A | 5/2000 | John |
| 6,083,249 A | 7/2000 | Familoni |
| 6,086,525 A | 7/2000 | Davey et al. |
| 6,091,977 A | 7/2000 | Tarjan et al. |
| 6,091,992 A | 7/2000 | Bourgeois |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| 6,146,335 A | 11/2000 | Gozani |
| 6,148,232 A | 11/2000 | Avrahami |
| 6,161,048 A | 12/2000 | Sluijter et al. |
| 6,169,924 B1 | 1/2001 | Meloy et al. |
| 6,205,359 B1 | 3/2001 | Boveja |
| 6,212,435 B1 | 4/2001 | Lattner et al. |
| 6,214,032 B1 | 4/2001 | Loeb et al. |
| 6,230,061 B1 | 5/2001 | Hartung |
| 6,240,316 B1 | 5/2001 | Richmond |
| 6,246,912 B1 | 6/2001 | Sluijter et al. |
| 6,266,564 B1 | 7/2001 | Hill et al. |
| 6,272,383 B1 | 8/2001 | Grey |
| 6,292,703 B1 | 9/2001 | Meier et al. |
| 6,319,241 B1 | 11/2001 | King |
| 6,332,089 B1 | 12/2001 | Acker |
| 6,341,236 B1 | 1/2002 | Osorio et al. |
| 6,345,202 B2 | 2/2002 | Richmond et al. |
| 6,356,784 B1 | 3/2002 | Lozano et al. |
| 6,356,788 B2 | 3/2002 | Boveja |
| 6,366,813 B1 | 4/2002 | Dilorenzo |
| 6,405,079 B1 | 6/2002 | Ansarinia |
| 6,442,432 B2 | 8/2002 | Lee |
| 6,445,953 B1 | 9/2002 | Bulkes et al. |
| 6,449,507 B1 | 9/2002 | Hill et al. |
| 6,456,878 B1 | 9/2002 | Yerich et al. |
| 6,463,328 B1 | 10/2002 | John |
| 6,473,644 B1 | 10/2002 | Terry, Jr. et al. |
| 6,496,729 B2 | 12/2002 | Thompson |
| 6,496,730 B1 | 12/2002 | Kleckner et al. |
| 6,582,441 B1 | 6/2003 | He et al. |
| 6,600,954 B2 | 7/2003 | Cohen |
| 6,600,956 B2 | 7/2003 | Maschino et al. |
| 6,606,521 B2 | 8/2003 | Paspa et al. |
| 6,610,713 B2 | 8/2003 | Tracey |
| 6,618,627 B2 | 9/2003 | Lattner et al. |
| 6,641,542 B2 | 11/2003 | Cho et al. |
| 6,682,480 B1 | 1/2004 | Habib et al. |
| 6,735,474 B1 | 5/2004 | Loeb et al. |
| 6,770,022 B2 | 8/2004 | Mechlenburg |
| 6,829,508 B2 | 12/2004 | Schulman |
| 6,839,594 B2 | 1/2005 | Cohen |
| 6,892,098 B2 | 5/2005 | Ayal |
| 6,907,295 B2 | 6/2005 | Gross et al. |
| 6,909,917 B2 | 6/2005 | Woods et al. |
| 7,025,730 B2 | 4/2006 | Cho et al. |
| 7,027,860 B2 | 4/2006 | Bruninga et al. |
| 7,047,076 B1 | 5/2006 | Li et al. |
| 7,149,575 B2 | 12/2006 | Ostroff et al. |
| 7,177,698 B2 | 2/2007 | Klosterman et al. |
| 7,190,998 B2 | 3/2007 | Shalev et al. |
| 7,212,867 B2 | 5/2007 | Van Venrooij et al. |
| 7,228,178 B2 | 6/2007 | Carroll |
| 7,277,749 B2 | 10/2007 | Gordon et al. |
| 7,289,853 B1 | 10/2007 | Campbell et al. |
| 7,324,852 B2 | 1/2008 | Barolat et al. |
| 7,324,853 B2 | 1/2008 | Ayal |
| 7,389,145 B2 | 6/2008 | Kilgore et al. |
| 7,483,752 B2 | 1/2009 | Von Arx et al. |
| 7,502,652 B2 | 3/2009 | Gaunt et al. |
| 7,532,932 B2 | 5/2009 | Denker et al. |
| 7,536,226 B2 | 5/2009 | Williams |
| 7,628,750 B2 | 12/2009 | Cohen |
| 7,630,771 B2 | 12/2009 | Cauller |
| 7,634,313 B1 | 12/2009 | Kroll et al. |
| 7,655,014 B2 | 2/2010 | Ko et al. |
| 7,657,311 B2 | 2/2010 | Bardy et al. |
| 7,657,322 B2 | 2/2010 | Bardy et al. |
| 7,660,632 B2 | 2/2010 | Kirby et al. |
| 7,680,538 B2 | 3/2010 | Durand et al. |
| 7,711,434 B2 | 5/2010 | Denker et al. |
| 7,736,379 B2 | 6/2010 | Ewers et al. |
| 7,780,625 B2 | 8/2010 | Bardy |
| 7,797,050 B2 | 9/2010 | Libbus et al. |
| 7,848,818 B2 | 12/2010 | Barolat et al. |
| 7,917,226 B2 | 3/2011 | Nghiem |
| 7,937,148 B2 | 5/2011 | Jacobson |
| 7,941,218 B2 | 5/2011 | Sambelashvili et al. |
| 7,974,706 B2 | 7/2011 | Moffitt et al. |
| 7,991,467 B2 | 8/2011 | Markowitz et al. |
| 7,996,089 B2 | 8/2011 | Haugland et al. |
| 7,996,092 B2 | 8/2011 | Mrva et al. |
| 8,019,443 B2 | 9/2011 | Schleicher et al. |

(56) References Cited

U.S. PATENT DOCUMENTS

| | | |
|---|---|---|
| 8,055,350 B2 | 11/2011 | Roberts |
| 8,075,556 B2 | 12/2011 | Betts |
| 8,090,438 B2 | 1/2012 | Bardy et al. |
| 8,115,448 B2 | 2/2012 | John |
| 8,131,377 B2 | 3/2012 | Shi et al. |
| 8,170,675 B2 | 5/2012 | Alataris et al. |
| 8,177,792 B2 | 5/2012 | Lubock et al. |
| 8,185,207 B2 | 5/2012 | Molnar et al. |
| 8,209,021 B2 | 6/2012 | Alataris et al. |
| 8,224,453 B2 | 7/2012 | De Ridder |
| 8,255,057 B2 | 8/2012 | Fang et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,396,559 B2 | 3/2013 | Alataris et al. |
| 8,428,748 B2 | 4/2013 | Alataris et al. |
| 8,463,404 B2 | 6/2013 | Levi et al. |
| 8,509,905 B2 | 8/2013 | Alataris et al. |
| 8,509,906 B2 | 8/2013 | Walker et al. |
| 8,554,326 B2 | 10/2013 | Alataris et al. |
| 8,634,927 B2 | 1/2014 | Olson et al. |
| 8,649,874 B2 | 2/2014 | Alataris et al. |
| 8,694,108 B2 | 4/2014 | Alataris et al. |
| 8,694,109 B2 | 4/2014 | Alataris et al. |
| 8,712,533 B2 | 4/2014 | Alataris et al. |
| 8,718,781 B2 | 5/2014 | Alataris et al. |
| 8,718,782 B2 | 5/2014 | Alataris et al. |
| 8,755,893 B2 | 6/2014 | Gross et al. |
| 8,768,472 B2 | 7/2014 | Fang et al. |
| 8,774,926 B2 | 7/2014 | Alataris et al. |
| 8,788,045 B2 | 7/2014 | Gross et al. |
| 8,792,988 B2 | 7/2014 | Alataris et al. |
| 8,849,410 B2 | 9/2014 | Walker et al. |
| 8,862,239 B2 | 10/2014 | Alataris et al. |
| 8,868,192 B2 | 10/2014 | Alataris et al. |
| 8,874,217 B2 | 10/2014 | Alataris et al. |
| 8,874,221 B2 | 10/2014 | Alataris et al. |
| 8,874,222 B2 | 10/2014 | Alataris et al. |
| 8,880,177 B2 | 11/2014 | Alataris et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,892,209 B2 | 11/2014 | Alataris et al. |
| 2002/0077554 A1 | 6/2002 | Schwartz et al. |
| 2002/0099419 A1 | 7/2002 | Cohen et al. |
| 2002/0124848 A1 | 9/2002 | Sullivan et al. |
| 2003/0040774 A1 | 2/2003 | Terry et al. |
| 2003/0060858 A1 | 3/2003 | Kieval et al. |
| 2003/0100933 A1 | 5/2003 | Ayal |
| 2003/0176898 A1 | 9/2003 | Gross et al. |
| 2004/0015205 A1 | 1/2004 | Whitehurst et al. |
| 2004/0019368 A1 | 1/2004 | Lattner et al. |
| 2004/0048795 A1 | 3/2004 | Ivanova et al. |
| 2004/0073270 A1 | 4/2004 | Firlik et al. |
| 2004/0167584 A1 | 8/2004 | Carroll et al. |
| 2004/0249431 A1 | 12/2004 | Ransbury et al. |
| 2004/0254624 A1 | 12/2004 | Johnson |
| 2005/0131495 A1 | 6/2005 | Parramon et al. |
| 2005/0143789 A1 | 6/2005 | Whitehurst |
| 2005/0165457 A1 | 7/2005 | Benser et al. |
| 2006/0100668 A1 | 5/2006 | Ben-David et al. |
| 2006/0155345 A1 | 7/2006 | Williams et al. |
| 2006/0271137 A1 | 11/2006 | Stanton-Hicks |
| 2007/0032827 A1 | 2/2007 | Katims |
| 2007/0067000 A1 | 3/2007 | Strother et al. |
| 2007/0067007 A1 | 3/2007 | Schulman et al. |
| 2007/0073354 A1 | 3/2007 | Knudson et al. |
| 2007/0083240 A1 | 4/2007 | Peterson et al. |
| 2007/0173893 A1 | 7/2007 | Pitts |
| 2008/0009914 A1 | 1/2008 | Buysman et al. |
| 2008/0021336 A1 | 1/2008 | Dobak |
| 2008/0027513 A1* | 1/2008 | Carbunaru ......... A61N 1/37223 607/60 |
| 2008/0039915 A1 | 2/2008 | Van Den Biggelaar |
| 2008/0103407 A1 | 5/2008 | Bolea et al. |
| 2008/0103572 A1 | 5/2008 | Gerber |
| 2008/0119911 A1 | 5/2008 | Rosero |
| 2008/0132964 A1 | 6/2008 | Cohen et al. |
| 2008/0269740 A1 | 10/2008 | Bonde et al. |
| 2009/0012590 A1 | 1/2009 | Inman et al. |
| 2009/0036975 A1 | 2/2009 | Ward et al. |
| 2009/0048642 A1 | 2/2009 | Goroszeniuk |
| 2009/0149912 A1 | 6/2009 | Dacey et al. |
| 2009/0152954 A1 | 6/2009 | Le et al. |
| 2009/0204170 A1 | 8/2009 | Hastings et al. |
| 2009/0204173 A1 | 8/2009 | Fang et al. |
| 2009/0270951 A1 | 10/2009 | Kallmyer |
| 2009/0281594 A1 | 11/2009 | King et al. |
| 2009/0326602 A1 | 12/2009 | Glukhovsky et al. |
| 2010/0094367 A1 | 4/2010 | Sen |
| 2010/0121405 A1 | 5/2010 | Ternes et al. |
| 2010/0125310 A1 | 5/2010 | Wilson et al. |
| 2010/0125313 A1 | 5/2010 | Lee et al. |
| 2010/0198298 A1 | 8/2010 | Glukhovsky et al. |
| 2010/0211131 A1 | 8/2010 | Williams et al. |
| 2010/0241195 A1 | 9/2010 | Meadows et al. |
| 2010/0249875 A1 | 9/2010 | Kishawi et al. |
| 2010/0280568 A1 | 11/2010 | Bulkes et al. |
| 2010/0305392 A1 | 12/2010 | Gross et al. |
| 2010/0312320 A1 | 12/2010 | Faltys et al. |
| 2010/0324630 A1 | 12/2010 | Lee et al. |
| 2011/0046696 A1 | 2/2011 | Barolat et al. |
| 2011/0093036 A1 | 4/2011 | Mashiach |
| 2011/0137365 A1 | 6/2011 | Ben-Erza et al. |
| 2011/0152965 A1 | 6/2011 | Mashiach |
| 2011/0160792 A1 | 6/2011 | Fishel |
| 2011/0160798 A1 | 6/2011 | Ackermann et al. |
| 2011/0208260 A1 | 8/2011 | Jacobson |
| 2011/0208271 A1 | 8/2011 | Dobak |
| 2011/0224744 A1 | 9/2011 | Moffitt et al. |
| 2011/0230922 A1 | 9/2011 | Fishel |
| 2011/0270339 A1 | 11/2011 | Murray et al. |
| 2011/0282412 A1 | 11/2011 | Glukhovsky et al. |
| 2011/0301662 A1 | 12/2011 | Bar-Yoseph et al. |
| 2011/0301670 A1 | 12/2011 | Gross |
| 2012/0004709 A1 | 1/2012 | Chen et al. |
| 2012/0010694 A1 | 1/2012 | Lutter et al. |
| 2012/0035679 A1 | 2/2012 | Dagan et al. |
| 2012/0041511 A1 | 2/2012 | Lee |
| 2012/0041514 A1 | 2/2012 | Gross et al. |
| 2012/0065701 A1 | 3/2012 | Cauller |
| 2012/0083857 A1 | 4/2012 | Bradley et al. |
| 2012/0101326 A1 | 4/2012 | Simon et al. |
| 2012/0123498 A1 | 5/2012 | Gross |
| 2012/0130448 A1 | 5/2012 | Woods et al. |
| 2012/0130463 A1 | 5/2012 | Ben-David et al. |
| 2012/0158081 A1 | 6/2012 | Gross et al. |
| 2012/0296389 A1 | 11/2012 | Fang et al. |
| 2013/0066393 A1 | 3/2013 | Gross et al. |
| 2015/0018728 A1 | 1/2015 | Gross et al. |
| 2015/0100109 A1 | 4/2015 | Feldman et al. |

FOREIGN PATENT DOCUMENTS

| | | |
|---|---|---|
| WO | 98/10832 | 3/1998 |
| WO | 99/26530 | 6/1999 |
| WO | 01/10375 | 2/2001 |
| WO | 01/10432 | 2/2001 |
| WO | 01/26729 | 4/2001 |
| WO | 02/09808 | 2/2002 |
| WO | 2004/064729 | 8/2004 |
| WO | 2006/102626 | 9/2006 |
| WO | 2007/019491 | 2/2007 |
| WO | 2009/055574 | 4/2009 |
| WO | 2009/110935 | 9/2009 |
| WO | 2011/154937 | 12/2011 |
| WO | 2012/012591 | 1/2012 |
| WO | 2013/035092 | 3/2013 |
| WO | 2013/111137 | 8/2013 |
| WO | 2013/164829 | 11/2013 |
| WO | 2014/081978 | 5/2014 |
| WO | 2014081978 | 5/2014 |
| WO | 2014/087337 | 6/2014 |
| WO | 2014/167568 | 10/2014 |

(56) References Cited

FOREIGN PATENT DOCUMENTS

| WO | 2014167568 | 10/2014 |
|----|------------|---------|
| WO | 2015/004673 | 1/2015 |
| WO | 2015004673 | 1/2015 |

OTHER PUBLICATIONS

C. de Balthasar, G. Cosendai, M. Hansen, D. Canfield, L. Chu, R. Davis, and J. Schulman, "Attachment of leads to RF-BION® microstimulators." Jul. 2005.

D.W. Eisele, A.R. Schwartz, and P.L. Smith, "Tongue neuromuscular and direct hypoglossal nerve stimulation for obstructive sleep apnea.," Otolaryngologic clinics of North America, vol. 36, 2003, p. 501.

G.E. Loeb, F.J.R. Richmond, J. Singh, R.A. Peck, W. Tan, Q. Zou, and N. Sachs, "RF-powered BIONs™ for stimulation and sensing," Engineering in Medicine and Biology Society, 2004. IEMBS'04. 26th Annual International Conference of the IEEE, 2005, pp. 4182-4185.

G.E. Loeb, F.J. Richmond, and L.L. Baker, "The BION devices: injectable interfaces with peripheral nerves and muscles," Neurosurgical focus, vol. 20, 2006, pp. 1-9.

E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.

A. Oliven, R.P. Schnall, G. Pillar, N. Gavriely, and M. Odeh, "Sublingual electrical stimulation of the tongue during wakefulness and sleep," Respiration physiology, vol. 127, 2001, pp. 217-226.

A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023.

A. Oliven, M. Odeh, L. Geitini, R. Oliven, U. Steinfeld, A.R. Schwartz, and N. Tov, "Effect of coactivation of tongue protrusor and retractor muscles on pharyngeal lumen and airflow in sleep apnea patients," Journal of Applied Physiology, vol. 103, 2007, p. 1662.

A.R. Schwartz, D.W. Eisele, A. Hari, R. Testerman, D. Erickson, and P.L. Smith, "Electrical stimulation of the lingual musculature in obstructive sleep apnea," Journal of Applied Physiology, vol. 81, 1996, p. 643.

W.H. Tran, G.E. Loeb, F.J.R. Richmond, a.C. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.

W.H. Tran, G.E. Loeb, F.J.R. Richmond, R. Ahmed, G.T. Clark, and P.B. Haberman, "First subject evaluated with simulated Biontm treatment in genioglossus to prevent obstructive sleep apnea," Engineering in Medicine and Biology Society, 2004. IEMBS'04. 26th Annual International Conference of the IEEE, 2005, pp. 4287-4289.

P.R. Troyk, "Injectable electronic identification, monitoring, and stimulation systems," Biomedical Engineering, vol. 1, 1999, p. 177.

T.K. Whitehurst, J.H. Schulman, K.N. Jaax, and R. Carbunaru, "The Bion® Microstimulator and its Clinical Applications," Implantable Neural Prostheses 1, 2009, pp. 253-273.

D.J. Young, "Wireless powering and data telemetry for biomedical implants," Engineering in Medicine and Biology Society, 2009. EMBC 2009. Annual International Conference of the IEEE, 2009, pp. 3221-3224.

Reid R. Harrison, et al., "Wireless Neural Recording with Single Low-Power Integrated Circuit", IEEE Trans Neural Syst Rehabil Eng. Aug. 2009; 17(4): 322-329.

An International Search Report and a Written Opinion both dated Apr. 17, 2012 which issued during the prosecution of Applicant's PCT/IL11/00870.

Patents Galore: Implantable Neurostimulators Fight Snoring and Corpse Eye-Proof Scanners. Printout from http://medgadget.com/2006/03/patents_galore.html (Downloaded Jan. 2012).

Chris Seper, "Neuros Medical Launches to Develop New Device to Block Amputee, Chronic Pain", Mar. 16, 2009.

Urgent® PC, Simple. Safe. Effective. Neuromodulation System, Uroplasty, Mar. 2009.

"JumpStart and Case Technology Ventures Invest in Neuros Medical", CTV Case Technology Ventures, Mar. 17, 2009.

"Responses to median and tibial nerve stimulation in patients with chronic neuropathic pain", by Theuvenet, Brain Topography, vol. 11, No. 4, 1999, pp. 305-313(9)—an abstract.

Armstrong, J, "Is electrical stimulation effective in reducing neuropathic pain in patients with diabetes?", by Foot Ankle Surg. Jul.-Aug. 1997; 36(4): 260-3—an abstract.

Ross Davis, Cerebellar Stimulation for Cerebral Palsy Spasticity, Function and Seizures. Clinical Neuroscience Center, 1999. pp. 290-299.

An Office Action dated Feb. 13, 2004, which issued during the prosecution of U.S. Appl. No. 10/254,024.

Bathien et al., Inhibition and synchronisation of tremor induced by a muscle twitch. J. Neurol, Neurosurg. And Psych. 1980, 43, 713-718.

Jobges et al., Vibratory proprioceptive stimulation affects Parkinsonian tremor. Parkinsonism & Related Disorders, 8(3), 171-176, Jan. 2002. (Abstract).

Mones and Weiss, The response of the tremor of patients with Parkinsonism to peripheral nerve stimulation. J. Neurol. Neurosurg. Psychiat. 1969, 32. 512-518.

Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.

N.J.M Rijkhoff, et al., "Selective Stimulation of Small Diameter Nerve Fibers in a Mixed Bundle", Proceedings of the Annual Project Meeting Sensations/Neuros and Mid Term Review Meeting Neuros, Apr. 21-23, 1999.

M. Manfredi, "Differential Block of conduction of larger fibers in peripheral nerve by direct current", Arch. Ital. Biol. 108:52-71, 1970.

A Restriction Requirement dated May 11, 2012, which issued during the prosecution of U.S. Appl. No. 12/946,246.

Cerebral Palsy, Barry S. Russman MD, CCurrent Science Inc. 2000.

A Notice of Allowance dated Mar. 7, 2005, which issued during the prosecution of U.S. Appl. No. 10/254,024.

A Notice of Allowance dated Aug. 26, 2004, which issued during the prosecution of U.S. Appl. No. 10/254,024.

An Office Action dated Jun. 24, 2011, which issued during the prosecution of U.S. Appl. No. 12/796,102.

An International Search Report and a Written Opinion both dated Nov. 14, 2011, which issued during the prosecution of Applicant's PCT/IL2011/000440.

An International Preliminary Report on Patentability dated Dec. 10, 2012, which issued during the prosecution of Applicant's PCT/IL2011/000440.

Provisional U.S. Appl. No. 60/263,834, filed Jan. 2, 2001.

Sweeney JD et al., "An asymmetric two electrode cuff for generation of unidirectionally propagated action potentials," IEEE Transactions on Biomedical Engineering, vol. BME-33(6) (1986).

An Office Action dated Apr. 9, 2012, which issued during the prosecution of U.S. Appl. No. 12/796,102.

Invitation to pay Additional Fees dated May 10, 2013 which issued during the prosecution of Applicant's PCT/IL2013/050069.

Naples GG et al., "A spiral nerve cuff electrode for peripheral nerve stimulation," by IEEE Transactions on Biomedical Engineering, 35(11) (1988).

Sweeney JD et al., "A nerve cuff technique for selective excitation of peripheral nerve trunk regions," IEEE Transactions on Biomedical Engineering, 37(7) (1990).

(56) References Cited

OTHER PUBLICATIONS

Ungar IJ et al., "Generation of unidirectionally propagating action potentials using a monopolar electrode cuff," Annals of Biomedical Engineering, 14:437-450 (1986).
Fitzpatrick et al., in "A nerve cuff design for the selective activation and blocking of myelinated nerve fibers," Ann. Conf. of the IEEE Eng. in Medicine and Biology Soc, 13(2), 906 (1991).
Rijkhoff NJ et al., "Orderly recruitment of motoneurons in an acute rabbit model," Ann. Conf. of the IEEE Eng., Medicine and Biology Soc., 20(5):2564 (1998).
Van den Honert C et al., "A technique for collision block of peripheral nerve: Frequency dependence," MP-12, IEEE Trans. Biomed. Eng. 28:379-382 (1981).
Baratta R et al., "Orderly stimulation of skeletal muscle motor units with tripolar nerve cuff electrode," IEEE Transactions on Biomedical Engineering, 36(8):83643 (1989).
Van den Honert C et al., "Generation of unidirectionally propagated action potentials in a peripheral nerve by brief stimuli," Science, 206:1311-1312 (1979).
M. Devor, "Pain Networks", Handbook of Brand Theory and Neural Networks, ED M.A. Arbib MIT Press pp. 696-701, 1998.
Epilepsy center. http://www.bcm.tmc.edu/neural/struct/epilep/epilpsy_vagus.html.
J.F. Cortese, "Vagus Nerve Stimulation for Control of Intractable Epileptic Seizures", May 31, 2001.
Evetovich T.K. et al., Gender comparisons of the mechanomyographic responses to minimal concentric and eccentric isokinetic muscle actions, Medicine & Science in Sports & Exercise, 1998 pp. 1697-1702. Abstract.
An Office Action dated Dec. 5, 2013, which issued during the prosecution of U.S. Appl. No. 13/528,433.
An Office Action dated Sep. 30, 2013, which issued during the prosecution of U.S. Appl. No. 12/796,102.
Chow et al., Evaluation of Cardiovascular Stents as Antennas for Implantable Wireless Applications, IEEE Transactions on Microwave Theory and Techniques, vol. 57, No. 10, Oct. 2009.
Dean, J. et al., "Motor Pattern Generation", Handbook of Brain Theory and Neural Networks, pp. 696-701.
Hu et al., Percutaneous Biphasic Electrical Stimulation for Treatment of Obstructive Sleep Apnea Syndrome, IEEE Transactions on Biomedical Engineering, Jan. 2008 vol. 55 Issue:1 p. 181-187—an abstract.
A. Oliven, Electrical stimulation of the genioglossus to improve pharyngeal patency in obstructive sleep apnea: comparison of resultsobtained during sleep and anesthesia, U.S. National Library of Medicine, National Institutes of Health May 2009;148(5):315-9, 350, 349—an abstract.
Mortimer et al., Peripheral Nerve and Muscle Stimulation, Neuroprosthetics Theory and Practice, Chapter 4.2, 2004, p. 632-638.
Muna Ebrish, Michael Etheridge, Kyle Friend, Forrest Johnson, Cardiovascular Stents as Antennas for Implantable Wireless Applications. BMEN 5151, Spring 2010.
Zabara J., Inhibition of experimental seizures in canines by repetitive vagal stimulation, Epilepsia. Nov.-Dec. 1992;33 (6):1005-12, http://www.ncbi.nlm.nih.gov/pubmed/1464256—an abstract.

A Notice of Allowance dated Jun. 9, 2014, which issued during the prosecution of U.S. Appl. No. 12/796,102.
Abkenari, Lara Dabiri, et al. "Clinical experience with a novel subcutaneous implantable defibrillator system in a single center." *Clinical Research in Cardiology* 100.9 (2011) 737-744.
An International Search Report and a Written Opinion both dated Jul. 11, 2013, which issued during the prosecution of Applicant's PCT/IL2013/050069.
An International Search Report and a Written Opinion both dated Apr. 29, 2014, which issued during the prosecution of Applicant's PCT/IB2013/060607.
An International Preliminary Report on Patentability dated Jul. 29, 2014, which issued during the prosecution of Applicant's PCT/IL2013/050069.
An International Preliminary Report on Patentability dated Jun. 9, 2015, which issued during the prosecution of Applicant's PCT/IB2013/060607.
Mitchum, A Shocking Improvement in Cardiology Science Life Blog, University of Chicago, http://sciencelife.uchospitals.edu/2010/04/13/a-shocking-improvement-in-cardiology/ (Downloaded Nov. 3, 2012).
https://www.uroplasty.com/files/pdf/20158.pdf Brochure (Downloaded Oct. 16, 2014).
Brindley (1983) A technique for anodally blocking large nerve fibers.
Provisional U.S. Appl. No. 60/985,353, filed Nov. 5, 2007.
Lind (2012) Advances in spinal cord stimulation.
Shealy (1967) Electrical inhibition of pain by stimulation of the dorsal columns.
Nov. 30, 2015 massdevice.com—St. Jude Medical's Proclaim Elite debuts in Europe.
Kaplan et al. (2009) Design and fabrication of an injection tool for neuromuscular microstimulators.
Supplementary European Search Report dated Dec. 22, 2014, which issued during the prosecution of Applicant's European App No. 11792044.7.
An Office Action dated Oct. 30, 2015, which issued during the prosecution of U.S. Appl. No. 14/226,723.
Zhang, Deyuan, et al. "Fabrication of graded TiN coatings on nitinol occluders and effects on in vivo nickel release." *Bio-medical materials and engineering* 18.6 (2008) (Abstract).
Takahata, Kenichi, et al. "Stentenna: a micromachined antenna stent for wireless monitoring of implantable microsensors." *Engineering in Medicine and Biology Society, 2003. Proceedings of the 25th Annual International Conference of the IEEE*. vol. 4. IEEE, 2003.
Kaszala, Károly, and Kenneth A. Ellenbogen. "Device sensing sensors and algorithms for pacemakers and implantable cardioverter defibrillators. "Circulation 122.13 (2010): 1328-1340.
Automatic Impedance Matching for 13.56 MHz NFC Antennas in Proceedings of the 6th Symposium on Communication Systems, Networks and Digital Signal Processing (2008) by Michael Roland, Harald Witschnig, Christian Saminger.
Office Action dated Nov. 21, 2016, in U.S. Appl. No. 14/601,626.
Office Action dated Dec. 12, 2016, in U.S. Appl. No. 14/939,418.

* cited by examiner

TRANSMITTING COILS FOR NEUROSTIMULATION

CROSS-REFERENCE TO RELATED APPLICATIONS

The present patent application is related to the following applications, filed on even date herewith:
(a) a US regular application entitled, "Extracorporeal Implant Controllers," to Oron et al., which was issued application Ser. No. 14/601,626; and
(b) a US regular application entitled, "Anchors and Implant Devices," to Oron et al., which was issued application Ser. No. 14/601,604.

Both of the above-mentioned applications are assigned to the assignee of the present application and incorporated herein by reference.

FIELD OF THE INVENTION

Applications of the present invention relate to apparatus and methods for transmitting power and/or data to an implanted medical device, e.g., a neurostimulation device.

BACKGROUND

Neurological disorders affect the nerves, muscles or the brain. Many neurological disorders reduce or eliminate voluntary recruitment of muscles, which may result in loss of ability to perform motor tasks or to maintain systems that depend on muscle activity for their function. Other disorders may cause pain to adjacent tissues.

Neurostimulation is a clinical tool used to treat various neurological disorders. This technique involves modulation of the nervous system by electrically activating fibers in the body.

SUMMARY OF THE INVENTION

Applications of the present invention include a medical implant, which includes a receiving coil. The medical implant receives power and/or data from a transmitting device, which includes first and second transmitting coils. To increase the power-transfer efficiency, the distance between the first and second transmitting coils is made to be approximately equal to the length of the receiving coil. To transmit power and/or data, a control unit in the transmitting device drives a current source to drive a current in a clockwise direction through one of the transmitting coils, and drive a current in a counterclockwise direction through the other one of the transmitting coils.

There is therefore provided, in accordance with some applications of the present invention, apparatus including:
a medical implant, including a receiving coil; and
a transmitting device, including:
a first transmitting coil;
a second transmitting coil disposed with respect to the first transmitting coil such that a shortest distance from an edge of the second transmitting coil to an edge of the first transmitting coil is within 20% of a length of the receiving coil;
a current source; and
a control unit configured to transmit power to the medical implant by driving the current source to:
drive a current in a clockwise direction through one of the first and second transmitting coils, and
drive a current in a counterclockwise direction through the other one of the first and second transmitting coils.

In some applications, the transmitting device further includes an at least partially rigid element connecting the first and second transmitting coils.

In some applications, a diameter of the first transmitting coil is within 5% of a diameter of the second transmitting coil.

In some applications, the diameters of the first and second transmitting coils are equal to one another.

In some applications, respective external diameters of the first and second transmitting coils are 20-50 mm.

In some applications, the length of the receiving coil is 3-30 mm.

In some applications, each of the first and second transmitting coils includes a plurality of turns surrounding an opening, a diameter of the opening being at least 70% of an external diameter of the transmitting coil.

In some applications, the diameter of the opening is at least 80% of the external diameter of the transmitting coil.

In some applications, the diameter of the opening is at least 90% of the external diameter of the transmitting coil.

In some applications,
the transmitting device includes a plurality of transmitting coils including:
the first and second transmitting coils; and
at least one additional transmitting coil,
the control unit being configured to select the first and second transmitting coils from the plurality of transmitting coils in response to a feedback signal received from the medical implant.

There is further provided, in accordance with some applications of the present invention, a method for transmitting power to a medical implant that includes a receiving coil, the medical implant being implanted at an implantation depth beneath a skin surface, the method including:
placing a first transmitting coil and a second transmitting coil adjacent to the skin surface, such that (a) a line connecting a center of the first transmitting coil to a center of the second transmitting coil is generally parallel to a central longitudinal axis of the receiving coil, and (b) a shortest distance from an edge of the first transmitting coil to an edge of the second transmitting coil is within 20% of a length of the receiving coil; and
transmitting power to the medical implant by:
driving a current in a clockwise direction through one of the first and second transmitting coils, and
driving a current in a counterclockwise direction through the other one of the first and second transmitting coils.

In some applications, the method further includes implanting the medical implant at the implantation depth.

In some applications, implanting the medical implant at the implantation depth includes implanting the medical implant such that the receiving coil is parallel to the skin surface.

In some applications, the method further includes selecting the first and second transmitting coils from a plurality of transmitting coils that includes (a) the first and second transmitting coils, and (b) transmitting coils that have diameters that are different from diameters of the first and second transmitting coils, in response to the implantation depth.

In some applications, selecting the first and second transmitting coils in response to the implantation depth includes selecting the first and second transmitting coils such that a mean radius of each of the first and second transmitting coils is within 15% of the implantation depth, the mean radius being a mean of an internal radius of the coil and an external radius of the coil.

In some applications, the method further includes transmitting data to the medical implant by driving the currents through the first and second transmitting coils.

In some applications, the first and second transmitting coils belong to a plurality of transmitting coils that includes at least one additional transmitting coil, and the method further includes:

placing the additional transmitting coils adjacent to the skin surface; and using a control unit, selecting the first and second transmitting coils from the plurality of transmitting coils in response to a feedback signal received from the medical implant.

The present invention will be more fully understood from the following detailed description of applications thereof, taken together with the drawings, in which:

DETAILED DESCRIPTION OF APPLICATIONS

Figure 1A:
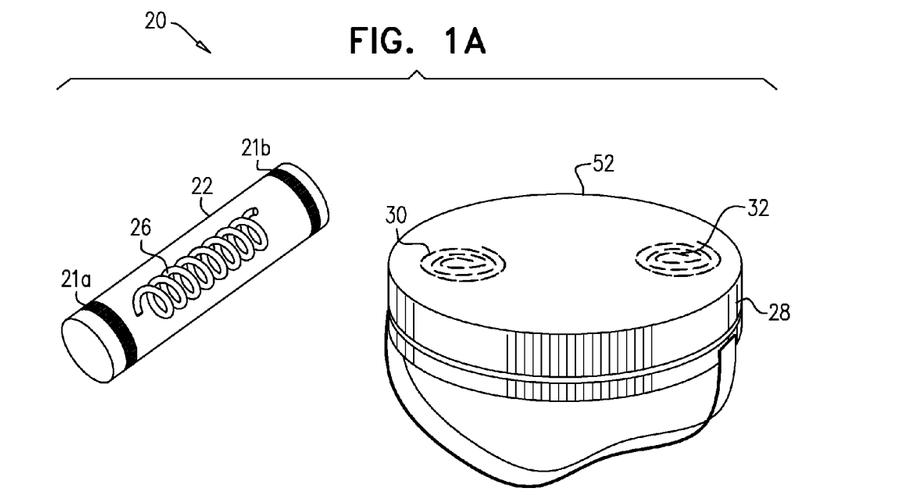
FIG. 1A is a schematic illustration of neurostimulation apparatus, in accordance with some applications of the present invention.
Figure 1B:
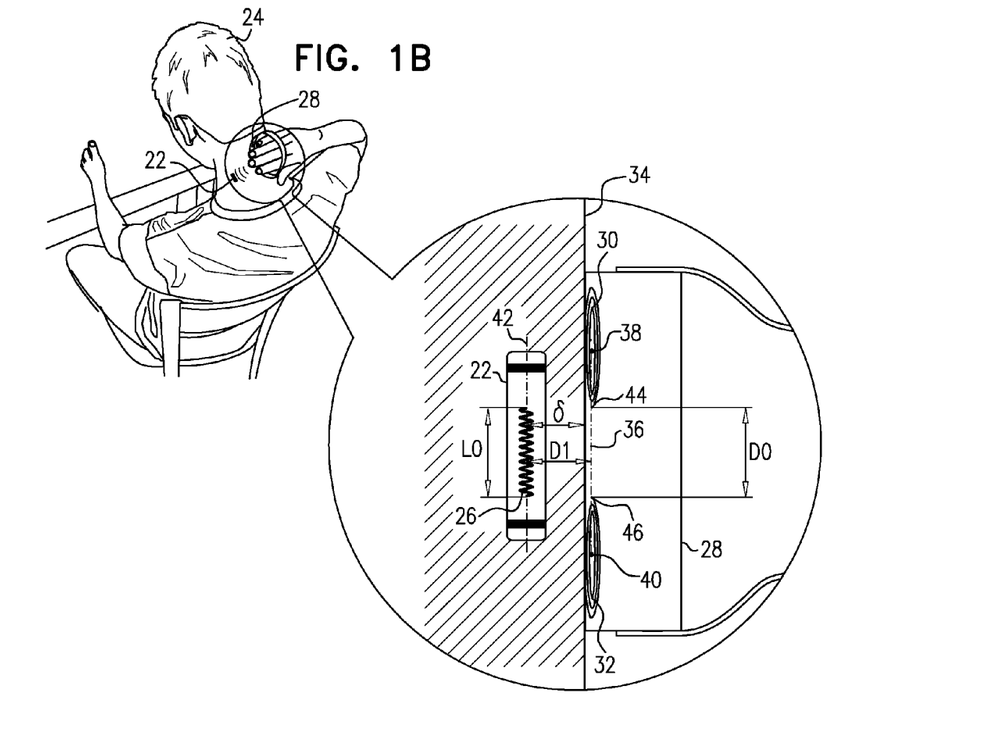
FIG. 1B depicts usage of neurostimulation apparatus, in accordance with some applications of the present invention.

Reference is made to FIG. 1A, which is a schematic illustration of neurostimulation apparatus 20, and to FIG. 1B, which depicts usage of apparatus 20, in accordance with some applications of the present invention. Apparatus 20 comprises a medical implant 22. Medical implant 22 comprises a receiving coil 26, which is configured to receive wirelessly-transmitted power and/or data from an external transmitter. Apparatus 20 further comprises a transmitting device 28, which is configured to transmit power and/or data to the medical implant.

In some applications, medical implant 22 is implanted in a subject 24 near a nerve, such as the vagus nerve. In response to the received power and/or data, the medical implant stimulates the nerve, e.g., via electrodes 21a and 21b. In other applications, the medical implant comprises a cardiac pacemaker. In response to the received power and/or data, the pacemaker controls the heartbeat of subject 24. In yet other applications, the medical implant comprises a spinal cord stimulator, which may comprise a lead having a plurality of electrodes that passes through a portion of the spinal column of the subject. In response to the received power and/or data, the stimulator stimulates the spinal cord of the subject.

Transmitting device 28 comprises a first transmitting coil 30 and a second transmitting coil 32. To transmit power and/or data to the medical implant, first transmitting coil 30 and second transmitting coil 32 are first placed adjacent to the skin surface 34. Subsequently, an alternating current is driven through the transmitting coils, as further described hereinbelow. (For transfer of data, the current is modulated.) The magnetic field that is generated by the alternating current induces a voltage in the receiving coil, thus effecting the transfer of power and/or data.

The inventors of the present invention have identified that in the context of applications of the present invention, the power-transfer efficiency may be improved by meeting certain conditions. (The power-transfer efficiency is the ratio of the amount of received power to the amount of transmitted power, and is proportional to the measure of magnetic coupling between the transmitting and receiving coils.) Accordingly, in some applications of the present invention, the transmitting coils are placed adjacent to the skin surface 34 such that (a) a line 36 connecting the center 38 of the first transmitting coil to the center 40 of the second transmitting coil is generally parallel to a central longitudinal axis 42 of receiving coil 26, and (b) a shortest distance D0 from an edge 44 of the first transmitting coil to an edge 46 of the second transmitting coil is relatively close to the length L0 of the receiving coil. Typically, to facilitate fulfilling the first condition, medical implant 22 is implanted such that the receiving coil is parallel to the skin surface. With respect to the second condition, it is noted that D0 may be within 40%, 35%, 30%, 25%, 20%, 15%, or 10% of L0. Typically, L0 is at least 3 mm and/or less than 30 mm, e.g., 3-30 mm.

In general, the expression "A is within x % of B," as used in the claims and description of the present application, indicates that A is greater or less than B by an amount that does not exceed x % of the larger of A and B. For example, with reference to the paragraph above, |D0−L0|/L0 and/or |D0−L0|/D0 may be less than 0.4, 0.35, 0.3, 0.25, or 0.2.

Although FIGS. 1A-B show receiving coil 26 integrated in a common unit with electrodes 21a and 21b, it is noted that the scope of the present invention includes a receiving coil that is separate from, but coupled to, the stimulating unit of the implant. For example, a receiving coil that is near the surface of the skin may be coupled via a wire to a cardiac pacemaker or a spinal cord stimulator.

Figure 2:
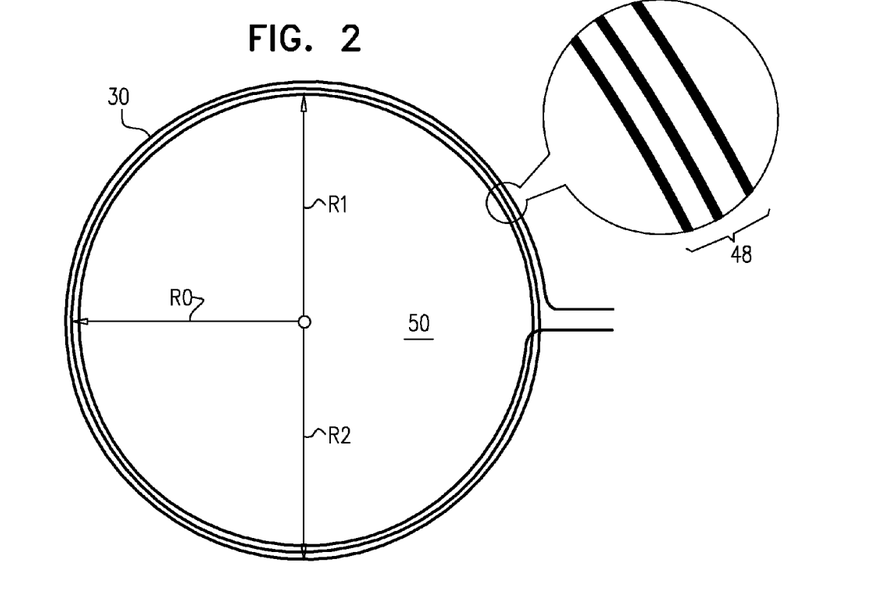
FIG. 2 is a schematic illustration of a transmitting coil, in accordance with some applications of the present invention.

Reference is now made to FIG. 2, which is a schematic illustration of transmitting coil 30, in accordance with some applications of the present invention. The inventors have deduced that the power-transfer efficiency is at least a function of (a) the distance D1 between axis 42 of the receiving coil and line 36 (FIG. 1B), which is typically approximately equal to the implantation depth delta of the receiving coil beneath the skin surface (FIG. 1B), and (b) the mean radii R0 of the transmitting coils. (As shown in the figure, mean radius R0 is a mean of an internal radius R1 of the coil and an external radius R2 of the coil.) In particular:

(i) For a fixed value of D1, the power-transfer efficiency reaches a maximum when R0 is approximately equal to D1; and (ii) For a fixed value of R0, the power-transfer efficiency increases as D1 decreases.

In some applications, in accordance with (i), transmitting coils that have a mean radius approximately equal to delta (which, as noted above, is approximately equal to D1) are selected, from a plurality of transmitting coils, as the first and second transmitting coils, the plurality of transmitting coils also including differently-sized transmitting coils. The first and second transmitting coils are typically selected such that the mean radii thereof are within 30%, 25%, or 20%, e.g., 15%, of delta. In other applications, all of the available transmitting coils have a mean radius that is approximately equal to the maximum expected implantation depth.

It is noted that for non-circular coils, a dimension that is generally equivalent to R0 takes the place of R0 with regards to the description above. For example, for a rectangular coil, the mean half-length of the side of the rectangle that is aligned with the central longitudinal axis of the receiving coil takes the place of R0, the mean half-length being the mean of the internal and external half-lengths of the coil. For an elliptical coil, the mean half-length of the axis of the ellipse that is aligned with the central longitudinal axis of the receiving coil takes the place of R0.

In some applications, transmitting device 28 comprises a plurality of transmitting coils having a variety of sizes. For example, the transmitting device may comprise several layers of transmitting coils, each layer including coils of a different size. In response to implantation depth delta, the physician activates only the coils of the appropriate size. Alternatively, control unit 56 may activate the coils of the appropriate size, in response to a feedback signal received from the medical implant. In other words, the control unit may cycle through different sizes, and in response to the feedback signal, choose the size that yields the maximum power-transfer efficiency. In general, the feedback mechanism is as described below, with reference to FIG. 5.

Typically, the external diameter 2*R2 of the first transmitting coil is close to the external diameter of the second transmitting coil; similarly, the internal diameters 2*R1 of the two coils are typically close to one another. For example, the corresponding diameters of the first and second transmitting coils may be within 15%, 10%, or 5% of one another, e.g., they may be equal. In some applications, the external diameters are at least 20 mm and/or less than 50 mm, e.g., 20-50 mm.

The inventors have identified that in the context of applications of the present invention, the power-transfer efficiency may be improved by keeping the turns 48 of each transmitting coil close to the perimeter of the coil; accordingly, R1 is typically relatively close to R2, e.g., R1 may be within 70%, 80%, or 90% of R2. Stated differently, each of the first and second transmitting coils comprises a plurality of turns 48 surrounding an opening 50, a diameter 2*R1 of the opening being at least 70%, 80%, or 90% of an external diameter 2*R2 of the transmitting coil.

Figure 3:
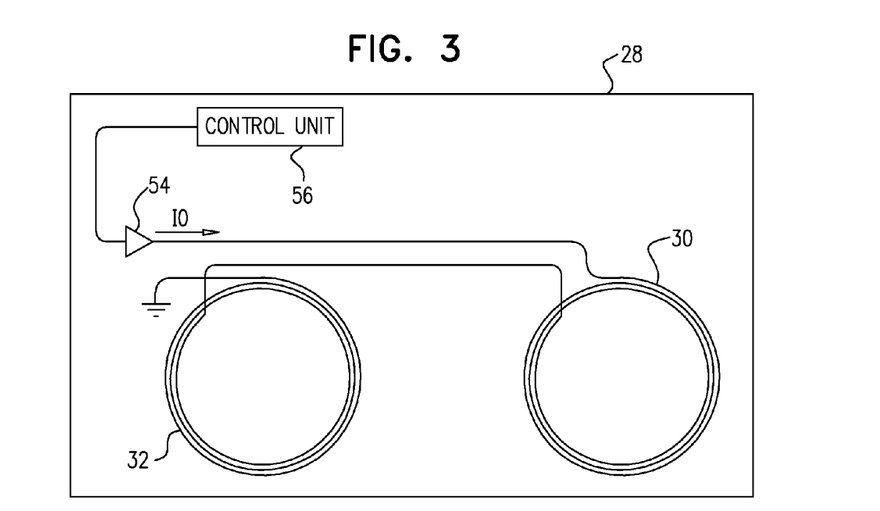
FIG. 3 is a schematic illustration of internal components of a transmitting device, in accordance with some applications of the present invention.
Figure 4:
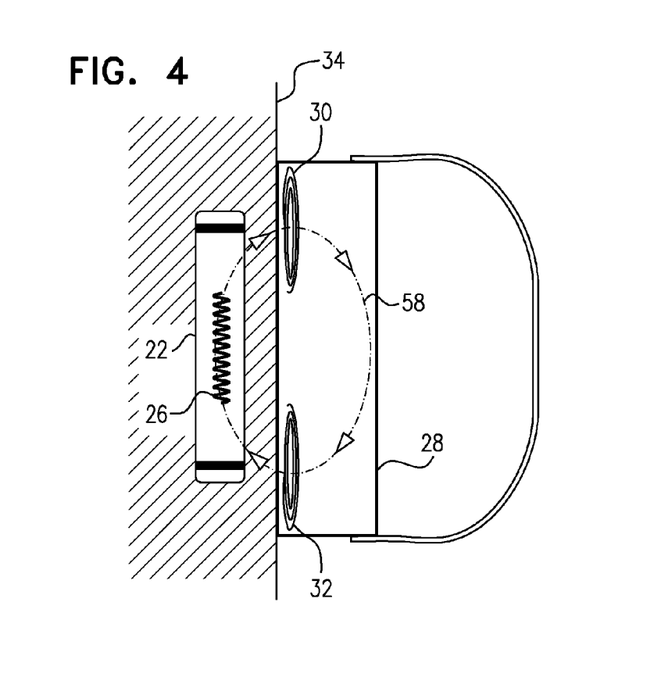
FIG. 4 shows a magnetic field line representing a magnetic field that is created in some applications of the present invention.

Reference is now made to FIG. 3, which is a schematic illustration of internal components of transmitting device 28, and to FIG. 4, which shows a magnetic field line 58 representing a magnetic field that is created by passing current through the transmitting coils, in accordance with some applications of the present invention.

In addition to the first and second transmitting coils, transmitting device 28 comprises a current source 54 and a control unit 56, which comprises, for example, a computer processor. Control unit 56 is configured to transmit power and/or data to the medical implant by driving current source 54 to drive an alternating current I0 through the first and second transmitting coils. Current I0 is driven in a clockwise direction through one of the transmitting coils, and in a counterclockwise direction through the other transmitting coil. The effect of the alternating current is to produce a magnetic field, which is depicted in FIG. 4. Due to the power-transfer-efficiency-improving positions, sizes, and/or orientations of the transmitting coils (as described hereinabove), the magnetic field at the receiving coil (represented by field line 58) is relatively strong, and is substantially aligned with the central longitudinal axis of the receiving coil. Thus, the magnetic field induces a relatively large amount of voltage in the receiving coil. It is noted that the first and second transmitting coils may be connected in series (as in FIG. 3) or in parallel with one another.

In some applications, the bottom surface 52 (FIG. 1A) of transmitting device 28 is flexible, such as, for example, to conform to the curvature of the neck. (In such applications, the transmitting coils may also flex.) For example, transmitting device 28 may take the form of a neck brace. In other applications, an at least partially rigid element, such as an at least partially rigid bottom surface 52, connects the first and second transmitting coils, such that flexure is generally limited. In general, the scope of the present invention includes, various degrees of flexibility/rigidity of bottom surface 52 and/or other parts transmitting device 28.

Figure 5:
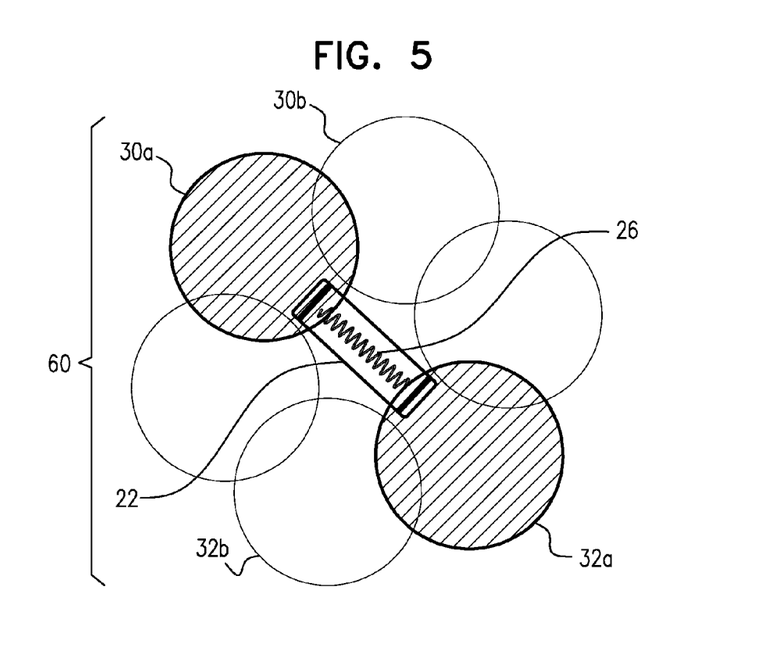
FIG. 5 is a schematic illustration of a plurality of transmitting coils placed over a medical implant, in accordance with some applications of the present invention.

Reference is now made to FIG. 5, which is a schematic illustration of a plurality 60 of transmitting coils placed over medical implant 22, in accordance with some applications of the present invention. In some applications, the transmitting device comprises a plurality 60 of transmitting coils that comprises the first and second transmitting coils and at least one additional transmitting coil. Plurality 60 of transmitting coils is placed adjacent to the skin surface. Control unit 56 then selects the first and second transmitting coils from plurality 60 in response to a feedback signal received from the medical implant, the feedback signal being indicative of an amount of power received by the medical implant, which in turn is indicative of the power-transfer efficiency. (The feedback signal may be transmitted by receiving coil 26 or by a separate antenna coupled to the medical implant. Similarly, the feedback signal may be received by one of transmitting coils 30 and 32, or by a separate antenna coupled to the transmitting device.) In other words, the control unit iterates over different pairs of coils, and selects the pair of coils that yields the maximum power-transfer efficiency.

For example, with reference to FIG. 5, the feedback signal may indicate that the power-transfer efficiency when using transmitting coils 30a and 32a is greater than when using any other pair of coils (e.g., coils 30b and 32b), since the magnetic field is most aligned with the central longitudinal axis of the receiving coil when using coils 30a and 32a. In response to the feedback signal, the control unit may select transmitting coils 30a and 32a as the first and second transmitting coils. This "optimization" process may also be used in situations in which the receiving coil is not parallel to the skin surface; by iterating over different pairs of coils, the pair of coils that yields the best-aligned magnetic field may be found.

It is noted that the configuration of plurality 60 that is shown in FIG. 5 is only one of many possible configurations included within the scope of the present invention.

In some applications, a physician implants the medical implant, and then transmits power and/or data to the implant as part of a training session, to show the subject how to use the apparatus.

As used in the present application, including in the claims, the "central longitudinal axis" of an elongate structure is the set of all centroids of cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.)

For some applications, apparatus and techniques described herein may be used in combination with one or more of those described in the following references, all of which are incorporated herein by reference:

U.S. Pat. No. 8,788,045 to Gross et al., filed Jun. 8, 2010, and entitled "Tibial Nerve Stimulation";

U.S. Pat. No. 8,755,893 to Gross et al., filed Mar. 14, 2013, and entitled "Tibial Nerve Stimulation";

PCT Patent Application Publication WO 2013/111137 to Gross et al., filed Jan. 24, 2013, and entitled "Wireless Neurostimulators";

PCT Patent Application Publication WO 2014/087337 to Gross et al., filed Dec. 3, 2013, and entitled "Delivery of Implantable Neurostimulators";

A US Patent Application to Oron et al., filed on even date herewith, and entitled "Anchors and Implant Devices," which was issued application Ser. No. 14/601,604; and A US Patent Application to Oron et al., filed on even date herewith, and entitled "Extracorporeal Implant Controllers," which was issued application Ser. No. 14/601,626.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   an implantable medical device, comprising a receiving coil; and
   a transmitting device, comprising:
      a first transmitting coil;
      a second transmitting coil disposed with respect to the first transmitting coil such that a shortest distance from an edge of the second transmitting coil to an edge of the first transmitting coil is within 20% of a length of the receiving coil;
      a current source; and
      a control unit configured to transmit power to the implantable medical device by driving the current source to:
         drive a current in a clockwise direction through one of the first and second transmitting coils, and
         drive a current in a counterclockwise direction through the other one of the first and second transmitting coils.

2. The apparatus according to claim 1, wherein the transmitting device further comprises an at least partially rigid element connecting the first and second transmitting coils.

3. The apparatus according to claim 1, wherein a diameter of the first transmitting coil is within 5% of a diameter of the second transmitting coil.

4. The apparatus according to claim 3, wherein the diameters of the first and second transmitting coils are equal to one another.

5. The apparatus according to claim 1, wherein respective external diameters of the first and second transmitting coils are 20-50 mm.

6. The apparatus according to claim 1, wherein the length of the receiving coil is 3-30 mm.

7. The apparatus according to claim 1, wherein each of the first and second transmitting coils comprises a plurality of turns surrounding an opening, a diameter of the opening being at least 70% of an external diameter of the transmitting coil.

8. The apparatus according to claim 7, wherein the diameter of the opening is at least 80% of the external diameter of the transmitting coil.

9. The apparatus according to claim 8, wherein the diameter of the opening is at least 90% of the external diameter of the transmitting coil.

10. The apparatus according to claim 1,
   wherein the implantable medical device is configured to transmit a feedback signal indicative of an amount of power received by the implantable medical device; and
   wherein the transmitting device comprises a plurality of transmitting coils comprising:
      the first and second transmitting coils; and
      at least one additional transmitting coil,
   the control unit being configured to receive the feedback signal, and select the first and second transmitting coils from the plurality of transmitting coils in response to the feedback signal.

11. A method for transmitting power to a medical implant that includes a receiving coil, the medical implant being implanted at an implantation depth beneath a skin surface, the method comprising:
   placing a first transmitting coil of a transmitting device and a second transmitting coil of the transmitting device adjacent to the skin surface, such that (a) a line connecting a center of the first transmitting coil to a center of the second transmitting coil is generally parallel to a longitudinal axis of the receiving coil, and (b) a shortest distance from an edge of the first transmitting coil to an edge of the second transmitting coil is within 20% of a length of the receiving coil; and
   using a control unit of the transmitting device, driving a current source of the transmitting device to transmit power to the medical implant by:
      driving a current in a clockwise direction through one of the first and second transmitting coils, and
      driving a current in a counterclockwise direction through the other one of the first and second transmitting coils.

12. The method according to claim 11, further comprising implanting the medical implant at the implantation depth.

13. The method according to claim 12, wherein implanting the medical implant at the implantation depth comprises implanting the medical implant such that the receiving coil is parallel to the skin surface.

14. The method according to claim 11, further comprising selecting the first and second transmitting coils from a plurality of transmitting coils that includes (a) the first and second transmitting coils, and (b) transmitting coils that have diameters that are different from diameters of the first and second transmitting coils, in response to the implantation depth.

15. The method according to claim 14, wherein selecting the first and second transmitting coils in response to the implantation depth comprises selecting the first and second transmitting coils such that a mean radius of each of the first and second transmitting coils is within 15% of the implantation depth,
   the mean radius being a mean of an internal radius of the coil and an external radius of the coil.

16. The method according to claim 11, further comprising transmitting data to the medical implant by driving the currents through the first and second transmitting coils.

17. The method according to claim 11, wherein:
   the medical implant is configured to transmit a feedback signal indicative of an amount of power received by the medical implant, the first and second transmitting coils belong to a plurality of transmitting coils that includes at least one additional transmitting coil, and the method further comprises:
   placing the additional transmitting coils adjacent to the skin surface; and
   using the control unit, receiving the feedback signal, and selecting the first and second transmitting coils from the plurality of transmitting coils in response to the feedback signal.

\* \* \* \* \*

UNITED STATES PATENT AND TRADEMARK OFFICE
CERTIFICATE OF CORRECTION

PATENT NO. : 9,597,521 B2
APPLICATION NO. : 14/601568
DATED : March 21, 2017
INVENTOR(S) : Anton Plotkin and Guri Oron It is certified that error appears in the above-identified patent and that said Letters Patent is hereby corrected as shown below:

On the Title Page

Under Inventors, please correct the second inventor from "Guri Oron" to --Gur Oron--

Signed and Sealed this
Twenty-seventh Day of September, 2022

Katherine Kelly Vidal
*Director of the United States Patent and Trademark Office*